US006458856B1

(12) United States Patent
Peng et al.

(10) Patent No.: US 6,458,856 B1
(45) Date of Patent: Oct. 1, 2002

(54) SEPARATION PROCESS FOR ONE-STEP PRODUCTION OF DIMETHYL ETHER FROM SYNTHESIS GAS

(75) Inventors: Xiang-Dong Peng, Orefield; Barry W. Diamond; Tsun-Chiu Robert Tsao, both of Allentown; Bharat Lajjaram Bhatt, Fogelsville, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/008,261

(22) Filed: Nov. 7, 2001

(51) Int. Cl.[7] .................. C07C 21/00; C07C 27/06; C07C 41/00
(52) U.S. Cl. .................. 518/700; 518/724; 518/725; 568/671; 568/698; 568/699
(58) Field of Search ................ 518/700, 724, 518/725; 568/671, 698, 699

(56) References Cited

U.S. PATENT DOCUMENTS

| 5,908,963 A | 6/1999 | Voss et al. .................. 568/671 |
| 6,147,125 A | 11/2000 | Shikada et al. ............. 518/713 |

FOREIGN PATENT DOCUMENTS

| CN | 1085824 A | 4/1994 | ............ B01J/27/14 |
| WO | 9623755 | 8/1996 | ........... C07C/41/01 |

OTHER PUBLICATIONS

"Catalyst and Process Development for Liquid Phase . . . ," Bhatt, B.L., et al, 17th Annual Intl. Pitt. Coal Conf., Sep. 2000.
Tianranqi Huagong, 24, Xie and Niu, (1999) p. 28.
"DME Production Tech. And Operation Results . . . ," Ohno, et al, Intl. DME Workshop, Japan, Sep. 7, 2000.

Primary Examiner—J. Parsa
(74) Attorney, Agent, or Firm—Robert J. Wolff

(57) ABSTRACT

An improvement to the process for separating dimethyl ether (DME) from byproducts in a one-step catalytic conversion of synthesis gas (syngas), the improvement comprising using a scrubbing solvent comprising a mixture of dimethyl ether and methanol for the separation of dimethyl ether and carbon dioxide from the unconverted synthesis gas in a scrubbing column. Additional improvements include recycling of the scrubbing solution, multi-step processing of the liquid effluent from the scrubber, and methods of processing the methanol-water effluent of the flash column that is interposed between the DME reactor and the scrubber.

13 Claims, 4 Drawing Sheets

SEPARATION PROCESS FOR ONE-STEP PRODUCTION OF DIMETHYL ETHER FROM SYNTHESIS GAS

BACKGROUND OF THE INVENTION

The present invention relates to a separation process for the one-step production of dimethyl ether (DME) from synthesis gas (syngas), a mixture of hydrogen ($H_2$) and carbon monoxide (CO). In the one-step syngas-to-DME process, syngas is converted in a single reactor (DME reactor) to methanol and DME over a catalyst system with methanol synthesis ($2H_2+CO \rightarrow CH_3OH$), methanol dehydration ($2CH_3OH \rightarrow DME+H_2O$), and water gas shift ($H_2O+CO \rightarrow CO_2+H_2$) activities. Due to a chemical synergy among these three reactions, the single pass syngas conversion in the DME reactor, or productivity, is significantly greater than that in a methanol synthesis reactor, wherein the methanol synthesis reaction primarily takes place. Since reactors for syngas conversion are expensive equipment for high-pressure operation at elevated temperatures, greater conversion or productivity means smaller DME reactors, associated equipment, and operation. This can reduce the cost in the syngas conversion part of the process, and possibly lead to a more economic process for DME production than the traditional two-step process, namely, methanol synthesis followed by methanol dehydration in two separate reactors.

However, the downstream separation for the one-step process could be costly because of the high volatility of two reaction products, DME and $CO_2$. $CO_2$ is especially a problem. In general, there are three ways to deal with the $CO_2$ problem. First, scrub out DME and methanol from the reactor effluent and let $CO_2$ remain in the unconverted syngas and build up in the DME reactor loop. $CO_2$ formation in the reactor will be suppressed when the $CO_2$ concentration in the reactor loop reaches a certain level. In this approach, the product stream entering the downstream separation process is $CO_2$ free, therefore it can be conducted at reasonable cost. However, this approach adversely affects the productivity of the DME reactor. Unless the $H_2$:CO ratio in the syngas feed to the DME reactor, is very high (e.g., >5, as in the WO Patent 96/23755 shown below), the final equilibrium $CO_2$ concentration in the DME reactor loop will be large. The presence of a large amount of $CO_2$ dilutes the reactants and hampers the synergy for the reaction system, resulting in a large decrease in the reactor productivity. One can avoid the build-up of a large amount $CO_2$ by operating in very $H_2$-rich (e.g., $H_2$:CO>5) regime. However, the productivity of the DME reactor in this regime is much lower than that when the DME reactor is operated in the optimal regime ($H_2$:CO around 1). It could even be lower than the productivity of a syngas-to-methanol reactor at its best-feed composition ($H_2$:CO=2) on a methanol equivalent basis. In brief, this suppressing-$CO_2$-formation approach can minimize the $CO_2$ handling cost; but it also takes away the very advantage of the one-step syngas-to-DME process—its high reactor productivity.

The second approach is to remove $CO_2$ from the unconverted syngas in the above approach before it is recycled to the DME reactor, thereby preserving the high productivity of the DME reactor. A commercially available $CO_2$ separation technology (physical or chemical absorption) can be used. However, since this requires an independent $CO_2$ separation system, the cost could be so high that it may negate all the cost saving from the high reactor productivity. Furthermore, in the natural gas-based syngas-to-DME process, $CO_2$ needs to be recycled to the syngas generation equipment to maintain a desired hydrogen:CO ratio. Since the pressure of the recovered $CO_2$ from these absorption units is low, the compressing cost for returning $CO_2$ to high-pressure syngas generation units will be high.

The third way to deal with the $CO_2$ problem is to make it an integral part of the downstream product separation process. $CO_2$ is removed, along with DME and methanol, from the reactor effluent. This would maintain the high productivity of the DME reactor, the very source of cost saving against the two-step DME process. The cost of the downstream separation will be higher than that of the two-step DME process due to the presence of $CO_2$. However, one may be able to develop optimized separation schemes so that the $CO_2$-induced cost will be much smaller than the cost saving by the high reactor productivity, therefore, warranting an economic one-step DME process. The objective of the current invention is to develop such an optimized separation scheme.

A number of separation schemes have been disclosed in the prior art for the one-step syngas-to-DME process. WO Patent 96/23755 and its equivalent U.S. Pat. No. 5,908,963 choose to avoid the $CO_2$ problem by operating a fixed bed syngas-to-DME reactor in a $H_2$-rich regime ($H_2$:CO>5). The reactor effluent is cooled in a condenser. The condensed reaction products, methanol, water and dissolved DME, are sent to two distillation columns for DME-methanol/water separation and methanol-water separation, respectively. Part of the gaseous stream from the condenser, containing unconverted syngas, DME and a small amount of $CO_2$, is recycled back to the DME reactor; the rest is sent to a scrubbing column to recover DME. Methanol, from the water-methanol column, is used as the scrubbing solvent. The DME-methanol mixture from the scrubbing column is fed to a methanol dehydration reactor. Due to the high $H_2$:CO ratio in the reactor feed, $CO_2$ formation is suppressed with a small amount of $CO_2$ (e.g., 3 mol. %) in the reactor loop. However, the reactor is operated in a regime far away from the optimal conditions.

Methanol is also used as the scrubbing solvent in separation scheme disclosed in a paper by Bhatt, Toseland, Peng and Heydorn, $17^{th}$ International Pittsburgh Coal Conference, Pittsburgh (September, 2000), for a 10 tons/day one step syngas-to-DME pilot plant (referred to as Bhatt's paper hereafter). In this separation scheme, the effluent from a slurry phase syngas-to-DME reactor is first cooled to condense methanol and water out. The rest of the effluent is fed to a scrubbing column which uses methanol as a solvent. All DME, methanol and $CO_2$ are removed from the unconverted syngas in the scrubbing column. The bottom stream from the scrubber is sent to a distillation column to regenerate methanol from DME and $CO_2$. Due to the trial nature of the work, the DME and $CO_2$ mixture was sent to flare without further separation.

A paper by Xie and Niu (Tianranqi Huagong, 24 (1999) p.28) examines different scrubbing solvents for DME separation, including methanol, water and methanol/water mixture. Methanol and 50/50 methanol/water mixture exhibited similar solubility to DME; both are better than pure water.

Chinese patent application No.1085824A to Guangyu et al. describes a downstream separation scheme for a one-step syngas-to-DME process. The water and methanol in the effluent from a fixed bed syngas-to-DME reactor are removed through a condenser and an absorption column, respectively. The rest of the reactor effluent enters into an extraction column. The unconverted syngas leaves the column from the top and is recycled to the DME reactor. A solvent is used in the extraction column to remove DME from the recycle stream. Water and ethanol are two solvents taught in the patent. When water is used as the extraction solvent, 5% of the $CO_2$ in the effluent gas is also dissolved in the water. The water solution is sent to a stripping-distillation column to recover product DME and regenerate water. When ethanol is used as the solvent, considerable amount of $CO_2$ (40%) is dissolved in the ethanol along with DME. The $CO_2$ from the bottom of the extraction column is first removed by some method (not specified). The rest is sent to a stripping-distillation column for DME-ethanol separation.

A downstream $CO_2$ separation scheme for a one-step syngas-to-DME process is described in a paper by Ohno, Ogawa, Shikada, Inoue, Ohyma, Yao and Kamijo, International DME Workshop, Japan (Sept. 7, 2000), (referred to hereafter as Ohno's paper). The DME reactor effluent is chilled to remove DME, $CO_2$ and methanol from the unconverted syngas, which is recycled to the DME reactor. The $CO_2$ in the condensed liquid is removed in a $CO_2$ column. The rest of the liquid is separated in a second column into product DME and methanol. The scheme also includes an amine-based absorption column to remove $CO_2$ from the syngas generated by an autothermal reformer before the syngas is fed to the DME reactor.

U.S. Pat. No. 6,147,125 to Shikada et al. discloses a downstream separation scheme for a one-step syngas-to-DME process. The methanol and water in the DME reactor effluent is condensed out first. The rest of the effluent is fed to a scrubbing column to remove DME and $CO_2$ from the unconverted syngas, which is recycled to the DME reactor. DME is used as the scrubbing fluid. The bottom of the scrubbing column is fed into a distillation column to separate $CO_2$ from DME.

With the exception of the schemes disclosed in WO patent application 96/23755 and the Ohno's paper, the other downstream separation schemes contain three common elements. First, a condenser is used to remove methanol and water from the reactor effluent. Second, a scrubber is used to remove DME and $CO_2$ from the unconverted syngas, which is recycled to the DME reactor. The third element includes two or three distillation columns for recovery of the scrubbing fluid and separation of $CO_2$, DME and, in some cases, methanol.

Scrubbing the volatiles (DME and $CO_2$) from unconverted syngas is a key step in the downstream separation scheme summarized above. Since the solubility of DME in all known solvents is greater than that of $CO_2$, the latter becomes the determining factor for the scrubbing operation, e.g., the amount of a solvent needed, the size of the scrubbing column. Therefore, it is the solubility of $CO_2$ in the scrubbing solvent that has a strong impact on the economics of the process. High solubility means smaller amount of scrubbing solvent, smaller size of the scrubbing column and other downstream columns that involve the scrubbing solvent. If cooling or chilling is needed to prepare the scrubbing solvent, high $CO_2$ solubility also means savings in the refrigeration cost.

The vapor pressure of the solvent also has significant impact on the economics. It is an important factor in determining the pressure and energy consumption of the downstream separation.

Water, methanol and DME have been used as the scrubbing solvent in the prior art, as described above. All three solvents have good solubility for DME but their solubility toward $CO_2$ varies considerably. Water is the poorest solvent for $CO_2$. When it is used as the scrubbing fluid, as in Chinese patent application No. 1085824A, most of the $CO_2$ remains in the unconverted syngas. This $CO_2$ needs to be either removed using an independent separation unit (e.g., physical or chemical absorption) or recycled to the DME reactor along with the unconverted syngas. This would either add additional separation cost or decrease the productivity of the DME reactor.

Methanol has very good solubility for DME. It is the scrubbing solvent for $CO_2$ removal in the commercial Rectisol process. It is also used in the process described in Bhatt's paper. However, $CO_2$ solubility in methanol is not optimum. A large amount of methanol must be chilled to −30 to −50 F. to scrub $CO_2$ from syngas effectively. This means a large capital investment for the scrubber and downstream distillation columns as well as a high operating cost for refrigeration.

DME has very good $CO_2$ solubility, translating into smaller scrubber and downstream separation columns. However, it has several shortcomings. First, because of the high vapor pressure of DME, the unconverted syngas stream leaving the scrubbing column will contain a significant amount of DME. This DME will act as a diluent in the DME reactor feed, decreasing its productivity. Second, the high volatility of DME requires the downstream separation process to be operated at high pressures for given column condenser temperatures. Third, the process built around pure DME as the scrubbing solvent does not allow any methanol, one of the products of the DME reactor, to enter the scrubbing column. Otherwise, the methanol needs to be recovered at the bottom of a distillation column. This means one needs to use a large amount of energy to evaporate all DME, the product part as well as the solvent part. To condense the solvent part back to liquid will also consume a lot of energy.

In summary, there are two important cost issues associated with the scrubbing solvent. The first issue is that high solubility toward $CO_2$ is desirable. Better solubility translates into a smaller scrubbing column, smaller downstream distillation columns and lower refrigeration duty. The second issue is the vapor pressure of the scrubbing fluid. Lower volatility means less negative impact on the DME reactor productivity and lower operating pressure for the downstream product separation section. Therefore, the ideal scrubbing solvent should have high solubility for $CO_2$ and low volatility. None of the solvents in the prior art possess both of these properties. DME is good at dissolving $CO_2$ but has high volatility. Methanol is less volatile but its solubility for $CO_2$ is much to be desired. The current invention provides a means for addressing the limitations of using either DME or methanol as the scrubbing solvent.

BRIEF SUMMARY OF THE INVENTION

In a general aspect, the process of the invention is an improvement in a process for production of dimethyl ether—in particular, for a process comprising the catalytic conversion of a synthesis gas in a dimethyl ether reactor, where the synthesis gas comprises a mixture of hydrogen and carbon monoxide, and the conversion results in an effluent mixture comprising dimethyl ether, methanol, carbon dioxide, water and unconverted synthesis gas, and wherein the effluent mixture is further processed to obtain a vapor mixture comprising dimethyl ether, carbon dioxide, and unconverted synthesis gas, and wherein that vapor mixture is processed by using a scrubbing solvent in a scrubbing column to separate both dimethyl ether and carbon dioxide from unconverted synthesis gas and wherein, subsequently, the diemethyl ether is separated from the carbon dioxide. The improvement comprises using, as the scrubbing solvent, a solvent comprising a mixture of dimethyl ether and methanol.

In a particular aspect of the invention, the effluent mixture is processed in a post-reactor flash column so as to produce the vapor comprising dimethyl ether, carbon dioxide, and unconverted synthesis gas, and said processing in the post-reactorflash column ("post-reactor" indicating after the reactor) also produces a liquid comprising methanol, water, dissolved dimethyl ether and carbon dioxide.

In some embodiments of the invention, part or all of the liquid produced by the post-reactor flash column is recycled back to the dimethyl ether reactor. In such embodiments, or in other embodiments, the process of the invention comprises directing a part or all of the liquid produced by the flash column to a methanol dehydration reactor, and then additionally:

producing a dehydration reactor mixture comprising dimethyl ether, carbon dioxide, methanol and water;

directing said dehydration reactor mixture to a post-dehydration flash column;

producing a vapor and a liquid in said post-dehydration flash column;

directing the vapor produced in said post-dehydration flash column to a DME-$CO_2$ column and therein separating DME of said vapor from $CO_2$ of said vapor;

directing the liquid produced in said post-dehydration flash column to a water-methanol column and therein separating methanol of said liquid from water of said liquid; and directing the methanol separated in the water-methanol column back to the methanol dehydration reactor.

In another aspect, related to the processing of liquid from the scrubbing column, the process of the invention further comprises:

directing the liquid stream from the scrubbing column to a post-scrubber flash column so as to produce a flash column vapor and a flash column liquid, said flash column vapor comprising dimethyl ether and carbon dioxide, said flash column liquid comprising a mixture of dimethyl ether and methanol, directing said flash column liquid to a solvent recovery column so as to produce a recovery column vapor and a recovery column liquid, said recovery column vapor comprising dimethyl ether and carbon dioxide, said recovery column liquid comprising a mixture of dimethyl ether and methanol, directing both the flash column vapor and the recovery column vapor to a DME-$CO_2$ column capable of separating DME from CO2, and directing the recovery column liquid to the scrubbing column so that said recovery column liquid becomes part of the scrubbing solvent in that column.

In a recycling aspect of the invention, the unconverted synthesis gas separated in the scrubbing column is recycled to the dimethyl ether reactor.

In another recycling aspect of the invention, the scrubbing solvent that exits the scrubbing column is recycled back to the scrubbing column, after being directed through one or more additional columns.

There are various preferred embodiments for carrying out the invention. In the scrubbing solvent, the molar fraction of dimethyl ether plus the molar fraction of methanol preferably equals at least 0.8, more preferably at least 0.95. Most preferably, the methanol and DME account for all of the scrubbing solvent except for trace elements (most typically less than one percent). In the scrubbing solvent, the ratio of dimethyl ether to methanol is preferably between 1/19 and 9, more preferably between 1/4 and 1, most preferably about 3/7. The effluent mixture is preferably cooled to 0 to 100° F., more preferably, to 20 to 60° F., as it exits the dimethyl ether reactor. The scrubbing solvent temperature in the scrubbing column is preferably between 0 and −60° F., more preferably between −20 and −50° F. The operating pressure of the scrubbing column is preferably between 300 and 1500 psig, more preferably between 400 and 900 psig. The operating pressure of the post-reactor flash column is preferably between 300 and 1500 psig, more preferably between 400 to 900 psig.

The liquid stream from the scrubbing column is preferably heated to a temperature between 50 and 250° F., more preferably between 100 and 200° F., prior to entering the post-scrubber flash column. The pressure of the post-scrubber flash column is preferably between 100 and 600 psig, more preferably between 300 and 500 psig. The pressure for the solvent recovery column range is preferably between 100 and 600 psig, more preferably between 300 and 400 psig. The pressure for the DME/CO2 distillation column is preferably between 100 and 400 psig, more preferably between 250 and 350 psig.

DETAILED DESCRIPTION OF THE INVENTION

Figure 1:
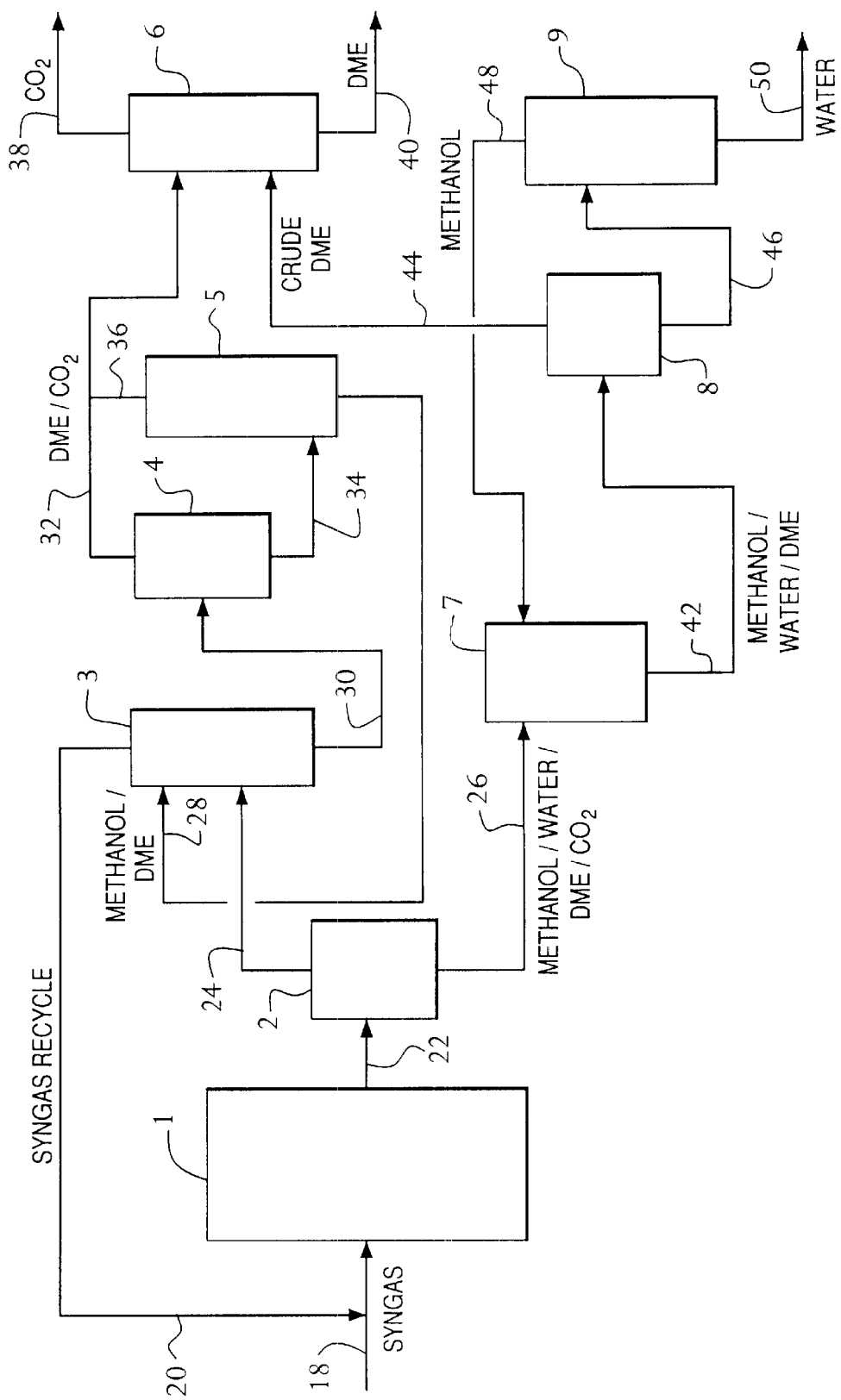
FIG. 1 is a block flow diagram of an embodiment of the present invention.

The current invention is an improved downstream separation scheme for the single-step syngas-to-DME process. It can be understood by reference to FIG. 1 FIG. 1 shows the block flowsheet diagram of a particular embodiment of the process of the invention. The synthesis gas 18 is typically not only comprised of its essential components, hydrogen and carbon monoxide, but also carbon dioxide, methane and inert species such as nitrogen. The synthesis gas 18 is converted to a mixture of DME, methanol, $CO_2$ and water in the DME reactor 1. The conversion can be achieved by any of a variety of methods, including the catalytic system described in U.S. Pat. No. 6,069,180 (Peng et al.) The DME reactor effluent 22, which contains both that mixture and unconverted syngas is cooled and fed to a high-pressure flash column 2 (also referred to herein as a post-reactor flash column.) The vapor phase containing DME, $CO_2$ and unconverted syngas 24, is passed through a scrubbing column 3.

A physical mixture 28 of methanol and DME is used as the scrubbing solvent to remove DME and $CO_2$ from the unconverted syngas 20, which is recycled to the DME reactor 1. The system is initially primed with a volume of scrubbing solvent. The DME/methanol ratio in the scrubbing solvent can be monitored and maintained at desired steady state. The bottom stream 30 from the scrubbing column 3 is fed to a medium-pressure flash column 4 (also referred to herein as a post-scrubber flash column) to flash off part of the $CO_2$ and DME dissolved in the solvent. The liquid stream 34 exiting the bottom of the medium-pressure flash column 4 contains all the scrubbing solvent and part of the product DME and $CO_2$. The scrubbing solvent component of the liquid stream 34 is recovered in a solvent-regeneration distillation column 5, cooled, and then recycled to the scrubbing column 3. The mixture 36 of DME and $CO_2$ from the top of the distillation column 5, combined with the vapor stream 32 from the top of the medium-pressure flash column 4, is fed to a DME-$CO_2$ distillation column 6 to separate $CO_2$ 38 from the product DME 40.

The bottom stream 26 from the high-pressure flash column 2 contains methanol, water and dissolved DME and CO2. The bottom stream 26 is sent to a methanol dehydration section, consisting of a dehydration reactor 7, a DME flash column 8 and a methanol-water distillation column 9. The methanol is converted to DME in the dehydration reactor 7 to form a mixture 42 of methanol, water, DME, and carbon dioxide, the carbon dioxide having come from the DME reactor. This mixture is sent to the DME flash column 8 (also referred to herein as a post-dehydration flash column) to flash off a crude DME 44 (i.e., DME mixed with carbon dioxide). The crude DME 44 is directed to the DME-$CO_2$ column 6 to separate the DME product 40 from $CO_2$ 38. The water 50 formed in the dehydration column 7 is discharged after being purified in the water-methanol column 9. Unconverted methanol 48 from the top of the water-methanol column 9 is recycled to the dehydration reactor 7.

The DME reactor effluent 22 is cooled to 0 to 100° F., preferably to 20 to 60° F. before entering the high-pressure flash column 2. The operating pressure of the high-pressure flash column 2 ranges from 300 to 1500 psig, preferably from 400 to 900 psig. The scrubbing solvent 28 consists of a physical mixture of methanol and DME. The molar fraction of DME in the solvent is between 0.05 and 0.9 (i.e., the molar ratio of DME to methanol is between 1/19 and 9), preferably between 0.2 and 0.5 (i.e., where the molar ratio of DME to methanol is between 1/4 and 1). The molar fraction of DME plus the molar fraction of methanol is preferably at least 0.8, more preferably at least 0.95. The solvent may also contain small amounts (less than 5%, more typically less than 1%) of other trace products from the DME reactor, such as $CO_2$, water, ethanol, methyl formate and other oxygenates. The solvent temperature ranges from 0 to −60° F., preferably from −20 to −50° F. The scrubbing column operates at high pressure, ranging from 300 to 1500 psig, preferably from 400 to 900 psig.

The bottom stream 30 from the scrubbing column is heated to 50 to 250° F., preferably from 100 to 200° F., before entering the medium pressure flash column 4. The pressure of the flash column ranges from 100 to 600 psig, preferably from 300 to 500 psig. The operating pressure for the solvent-regenerating column 5 ranges from 100 to 600 psig, preferably from 300 to 400 psig. The operating pressure for the DME/$CO_2$ column 6 is between 100 to 400 psig, preferably from 250 to 350 psig. The selection of an elevated pressure for the DME/$CO_2$ column is based on two considerations. First, it keeps the DME product in the liquid form at a reasonable temperature. Second, it reduces the compressing cost if the recovered $CO_2$ is to be recycled to the syngas generation unit or fed to a power generation gas turbine.

Figure 2:
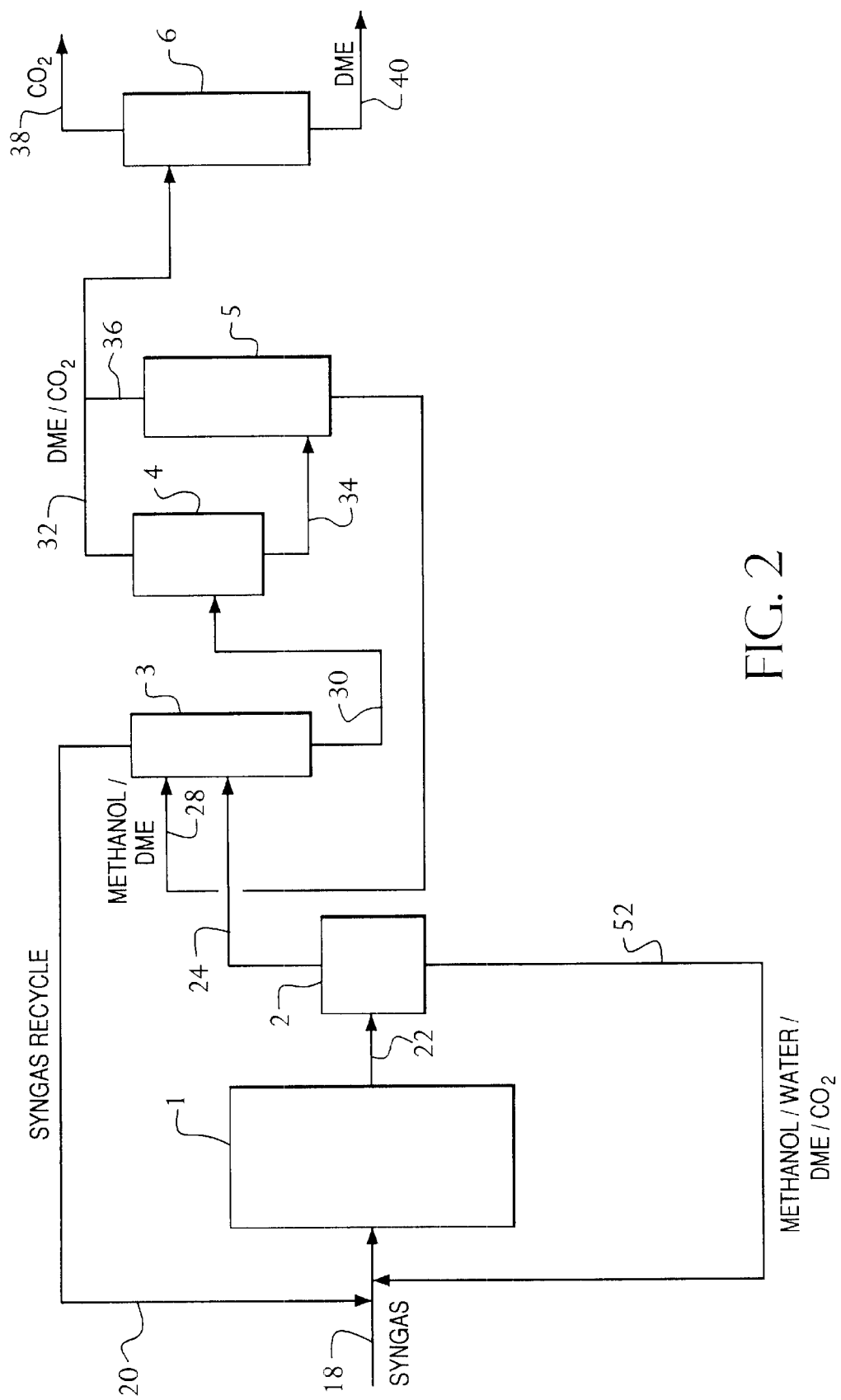
FIG. 2 is a block flow diagram of another embodiment of the present invention. The methanol-containing liquid stream is recycled to the DME reactor instead of being sent for a dehydration in a separate section as in FIG. 1.
Figure 3:
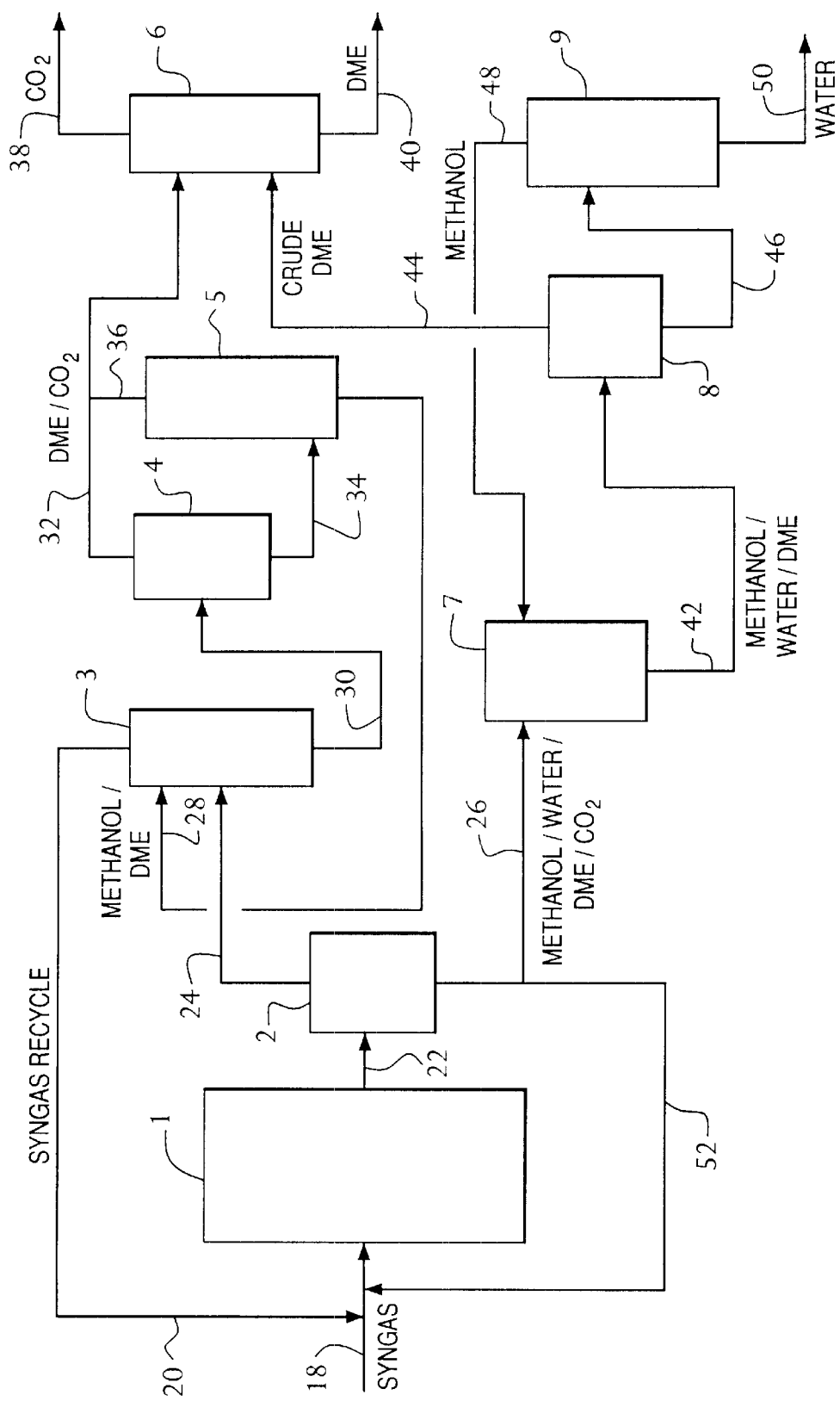
FIG. 3 is a block flow diagram of another embodiment of the present invention. The methanol-containing liquid stream is split in two parts, wherein one part is recycled to the DME reactor and another part is sent for a dehydration in a separate section.

There are three modes of operation for the liquid stream 26 from the high-pressure flash column 2, containing methanol, DME, water and a small amount of $CO_2$. In the first mode, the stream 26 is fed to a dehydration methanol reactor 7, as shown in FIG. 1. Alternatively, in a second mode, the stream 26 can simply be recycled to the DME reactor 1 as illustrated by FIG. 2. The third mode is a combination of the first two modes as illustrated in FIG. 3. In the third mode, the liquid stream is split such that one part 52 of the stream is recycled to the DME reactor 1, and another part 26 is fed to the dehydration reactor 7. The choice of the mode of operation depends on the methanol content in the DME reactor effluent. The first mode becomes more preferred as the methanol content of the liquid stream becomes larger.

The methanol dehydration reactor 7 is a conventional fixed bed reactor using a solid acid material as the dehydration catalyst. It operates at a pressure between 100 to 600 psig, preferably between 200 to 400 psig. The temperature ranges from 300 to 700° F., preferably from 400 to 600° F. The operating temperature and pressure for the DME flash column 8 are 100 to 300° F. and 100 to 400 psig, respectively. The water-methanol column 9 operates at a pressure range between 50 and 300 psi, preferably between 100 and 200 psig.

The advantages and uniqueness of the current invention lie in part in a new type of scrubbing solvent, whose essential feature is that it comprises a mixture of methanol and DME. The solvent has greater $CO_2$ solubility than pure methanol because of the presence of DME. Yet, it does not have the high vapor pressure that pure DME has because DME is dissolved in methanol. The unique properties of the mixed solvent have a major impact on the economics of the syngas-to-DME process.

Figure 4:
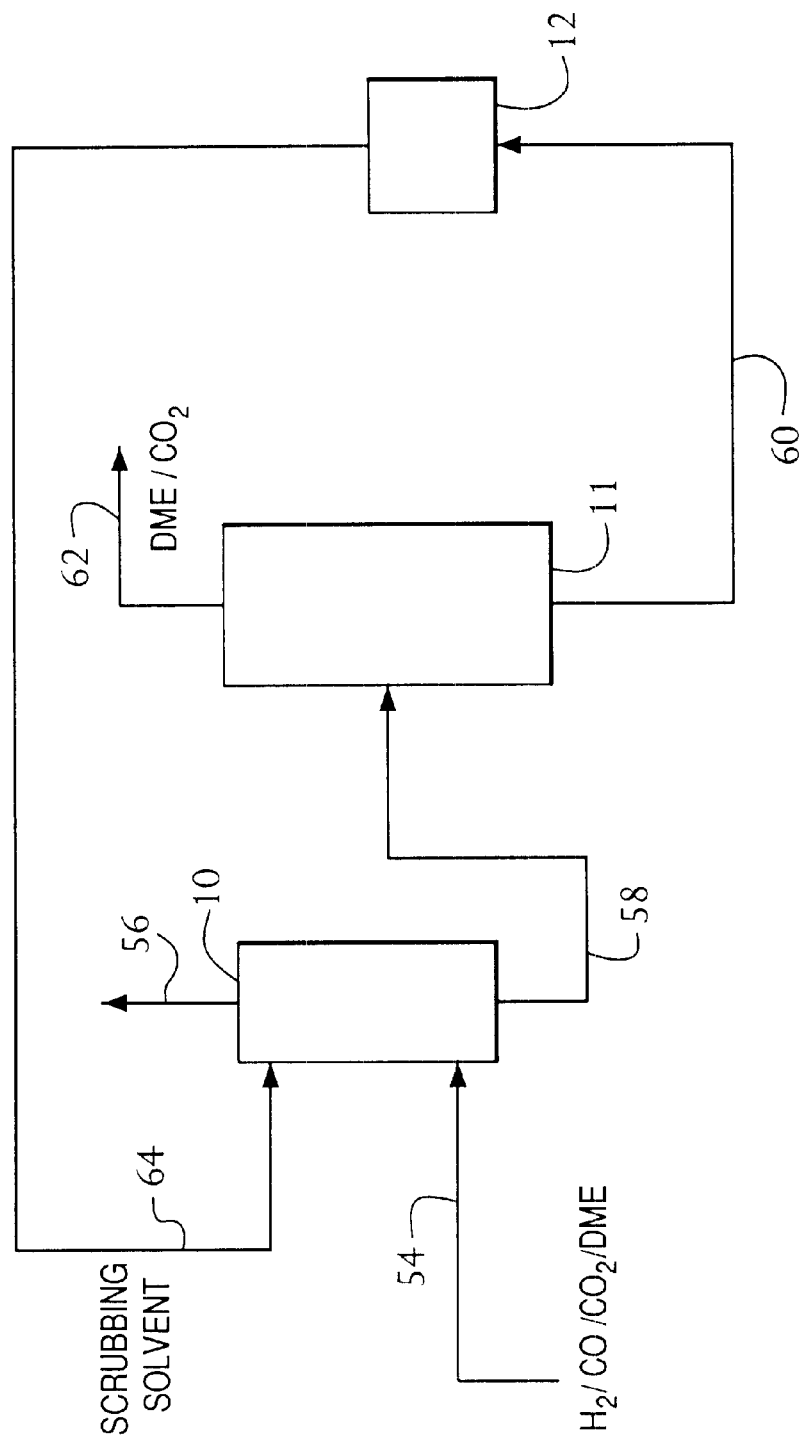
FIG. 4 illustrates a flow scheme that can be used to demonstrate the advantages of is using the methanol/DME mixture of the present invention as the scrubbing solvent, instead of using pure methanol or pure DME as done in the prior art.

The flow scheme shown in FIG. 4 is designed to illustrate the advantages of using the methanol/DME mixture as the scrubbing solvent as compared to the two solvents taught in the prior art, pure methanol and pure DME. A gas stream 54 simulating a DME reactor effluent at 50° F. is fed to a scrubbing column 10. The stream contains 4000 lbmol/hr of $H_2$; 4000 lbmol/hr of CO, 1000 lbmol/hr of $CO_2$ and a variable amount of DME (832–1270 lbmol/hr). The column 10 is set to scrub the same amount of $CO_2$ and DME from the gas stream for the three different solvents so that the production case is more realistically represented and the downstream separation processes for the different solvents can be compared on a consistent basis. This is achieved using different amount of a solvent and adjusting the DME amount in the gas stream. As shown below, the DME content in the gas stream is highest in the pure DME case and lowest in the pure methanol case. This is a real reflection of how much DME is in the reactor recycle loop due to different DME vapor pressures for different solvents. The bottom stream 58 from the scrubbing column 10 is heated to 150° F. and sent to a distillation column 11 to regenerate the solvent. The same $CO_2$ and DME recovery (both around 99.9%) is used for the three different solvents. Furthermore, the condenser temperature is fixed at 120° F. by adjusting the column pressure. The regenerated solvent 60 is cooled and chilled from 20 to −30° F. through a chiller 12 and the chilled regenerated solvent 64 is recycled to the scrubbing column 10. This is a simplified model process to be used to illustrate the economic impact of a scrubbing solvent only.

The following parameters from this process are used for semi-quantitative evaluation of different solvents. The molar flow of a solvent to the scrubbing column indicates its solubility toward $CO_2$. The diameter of the scrubbing column relates to its capital cost. The economic impact on the solvent regeneration column is shown by 5 parameters: the diameter of the column, the pressure of the column, the condenser heat duty and the reboiler temperature and heat duty. The cooling duty of the chiller relates to the refrigeration cost for each solvent. Finally, the molar fraction of DME in the gas stream leaving the scrubbing column is related to its negative effect on the productivity of the DME reactor, since the DME will serve as a diluent to the reactor feed.

The data generated for following examples is the result of using a process simulation computer program in connection with the system diagramed in FIG. 4.

EXAMPLE 1

A methanol/DME mixture, in which the molar per cent ratio of methanol:DME is 70-30, is used as the solvent for the scrubbing column 10. The amount of DME in the gas stream to the scrubbing column is 1000 lb-mol/hr. The amount of $CO_2$ and DME scrubbed in the column is 834 lb-mol/hr and 832 lb-mol/hr, respectively. The performing and economic parameters described above for the solvent are listed in Table 1.

Comparative Example 1

Pure methanol is used as the solvent for the scrubbing column 10. The amount of DME in the gas stream to the scrubbing column is 832 lb-mol/hr. The amount of $CO_2$ and DME scrubbed in the column is 840 lb-mol/hr and 832 lb-mol/hr, respectively. The performing and economic parameters described above for the solvent are listed in Table 1.

Comparative Example 2

Pure DME is used as the solvent for the scrubbing column 10. The amount of DME in the gas stream to the scrubbing column is 1270 lbmol/hr. The amount of $CO_2$ and DME scrubbed in the column is 834 lbmol/hr and 833 lbmol/hr, respectively. The performing and economic parameters described above for the solvent are listed in Table 1.

TABLE 1

The performance and economic parameters for different scrubbing solvents.

| | solv. mol. flow | CH. heat duty | SC. diam | REG. diam | REG. press. (PSI) | CON. heat duty | REB. temp. (F) | REB. heat duty | % mol. DME in SC. off-gas |
|---|---|---|---|---|---|---|---|---|---|
| 70-30 mixt. | 1 | 1 | 1 | 1 | 370 | 1 | 280 | 1 | 2.1 |
| Pure MEOH | 1.3 | 1.1 | 1 | 1.3 | 360 | 10.5 | 352 | 3.0 | 0 |
| Pure DME | 0.64 | 0.8 | 1 | 1.3 | 410 | 5.3 | 199 | 1.1 | 5.3 |

Legend to Table 1:
CH.—chiller; SC.—scrubber; CON.—condenser; REG.—regenerator; REB.—reboiler; mol.—molar; mixt.—mixture; press.—pressure; diam—diameter, solv.—solvent;

Judging by all parameters, the methanol/DME mixture is a better solvent than pure methanol. Its solubility toward $CO_2$ is 30% greater than pure methanol. This leads to 10% lower refrigeration duty. Its effect on the size of the scrubbing fluid is minimal mainly because the pure methanol has higher density; therefore, the volumetric flows of the two solvents are similar. The most significant is the impact on the solvent regeneration column. Since $CO_2$ is more volatile than DME, recovering DME from the solvent is the operation that determines the operating characteristics of the column. In the pure methanol case, this is a deep recovery that requires reboiling a large amount of methanol. This results in large reboiler heat duty, which in turn leads to large condenser duty. It also leads to large column diameter because of large reboiler vapor and reflux flow. When the methanol/DME mixture is used, this deep DME recovery becomes a simple fractionation. This decreases the condenser duty by a factor of 10.5, the reboiler duty by a factor of 3, and the column diameter by 21%. All these translate into much lower capital and operating costs. The only advantage that pure methanol has is zero escape of DME from the scrubbing column. This will have some positive effect on the productivity of the DME reactor.

Although there are clear advantages to the present invention, there are also trade-offs between the methanol/DME mixture and pure DME as the scrubbing solvent. In terms of saving refrigeration cost, the methanol/DME mixture does not have any advantages over pure DME. The greater $CO_2$ solubility by pure DME actually requires 20% less refrigeration. As to the size of the scrubbing column, the trade-off between molar flow and the density of the solvent makes it even for the two solvents.

The economics associated with the regeneration column is in favor of the methanol/DME mixture. Since the $CO_2$/DME mixture in the pure DME-as-solvent case is more volatile than the $CO_2$/DME/methanol mixture in the mixture-as-solvent case, the column pressure for the pure DME case is 40 psi greater than that for the mixture case. Furthermore, a greater reflux ratio is needed in the pure DME case, again due to its high volatility. This results in 4.3 times greater condenser duty and 27% greater column diameter.

The other considerations also favor the methanol/DME mixture as the scrubbing solvent. The high DME vapor pressure in the scrubbing column in the pure DME case leads to a 5.3% DME in the gas stream leaving the scrubbing column, as opposed to 2.1% in the mixture case. This DME will serve as a diluent to the DME reactor feed, decreasing its productivity. Finally, the methanol/DME mixture case has more operational flexibility than the pure DME case. For example, the mixture case can allow methanol, a product of the DME reactor, to be present in the gas stream to the scrubbing column, since this methanol can be readily recovered from the bottom stream of the solvent regeneration column. In the pure DME case, to recover this methanol, one needs to evaporate all DME, product plus solvent, which requires a large amount of energy consumption. It will consume even more energy to condense and cool the solvent part of the DME to the scrubbing conditions (e.g., −30° F. liquid).

While the major advantages and uniqueness of the current invention reside in the special type of solvent used for the scrubber, the process also contains other unique features that have positive economic effects. One such feature is the scheme associated with the $CO_2$/DME separation column. It is more costly if $CO_2$ and DME separation is performed simultaneously in the solvent regeneration column, i.e., collecting DME in a side stream. This is because any reboiling and refluxing necessary to achieve this separation will not only deal with $CO_2$ and the product part of the DME, but also with the solvent, which is in large excess compared to $CO_2$ and the product DME. Furthermore, the dedicated $CO_2$-DME column makes it economically advantageous to use the medium-pressure flash column, which precedes the solvent regeneration column, and the DME flash column in the dehydration section of the process. The medium-pressure flash reduces the load of the solvent regeneration column considerably. The DME flash column 8 reduces the recycle flow in the methanol dehydration loop, therefore decreasing the sizing and operating cost of the dehydration reactor 7, the water-methanol column 9 and the recycle compression. While columns 4 and 5 provide economic benefits, their vapor streams 32 and 36, respectively, contain both $CO_2$ and DME and require further separation. This separation can be accomplished in the $CO_2$-DME column 6 without invoking another separation unit. No such integration has been disclosed in the prior art.

Another important feature of the present proposed scheme is to feed condensables from the high-pressure flash column directly to a downstream methanol dehydration section. This is especially important when a large amount of methanol is produced in the DME reactor, for example, due to the feed gas composition and/or the catalyst selectivity. Otherwise, this stream needs to be recycled to the DME reactor and methanol will build up in this recycle loop. Although this will save all the cost associated with a separate dehydration section, it will reduce the productivity of the DME reactor significantly. Considering that the gas flow in the DME synthesis loop is at least one order of magnitude greater than that in the dehydration section, the overall economic impact of recycling a large amount of methanol in the DME synthesis loop will be negative. Using a separate dehydration section provides another degree of freedom for maximizing the DME reactor productivity, therefore, optimizing the economics of the process. The scheme of how this condensed stream is introduced to the dehydration reactor and the integration of the dehydration section with the $CO_2$-DME separation have not been taught in the prior art.

Additional advantages of the present invention are a result of the high pressure (about 300 psig) of the carbon dioxide as it exits from the $CO_2$-DME column. This high pressure carbon dioxide can profitably be recycled to the syngas generator that is the source of the syngas for the process. Alternatively, It can be profitably used in a power generator gas turbine.

A scrubbing solvent is usually a pure fluid. Using a mixture as the scrubbing solvent in the current invention addresses the following needs: to maximize the productivity of the DME reactor; to remove $CO_2$ from the DME reactor recycle stream; to deal with $CO_2$ removal as an integral part of the downstream separation; to minimize the refrigeration associated with chilling the scrubbing fluid; to reduce the volatility of the scrubbing solvent; and to carry out a fractionation other than by a deep recovery in the solvent regeneration column.

Although illustrated and described herein with reference to certain specific embodiments, the present invention is not intended to be limited to the detailed embodiments shown. One skilled in the art can understand the invention and make various modifications thereto without departing from the basic spirit thereof, and without departing from the scope of the claims which follow.

What is claimed is:

1. In a process for production of dimethyl ether, said production comprising the catalytic conversion of a synthesis gas in a dimethyl ether reactor, said synthesis gas comprising a mixture of hydrogen and carbon monoxide, said conversion resulting in an effluent mixture comprising dimethyl ether, methanol, carbon dioxide, water and unconverted synthesis gas, wherein said effluent mixture is further processed to obtain a vapor mixture comprising dimethyl ether, carbon dioxide, and unconverted synthesis gas, and wherein said vapor mixture is processed by using a scrubbing solvent in a scrubbing column to separate both dimethyl ether and carbon dioxide from unconverted synthesis gas, and wherein the dimethyl ether is subsequently separated from the carbon dioxide; the improvement comprising using, as the scrubbing solvent, a solvent comprising a mixture of dimethyl ether and methanol.

2. A process of claim 1 wherein, in the scrubbing solvent, the molar fraction of dimethyl ether plus the molar fraction of methanol equals at least 0.8.

3. A process of claim 2 wherein, in the scrubbing solvent, the molar ratio of dimethyl ether to methanol is between 1/19 and 9.

4. A process of claim 3 wherein, in the scrubbing solvent, the molar ratio of dimethyl ether to methanol is between 1/4 and 1.

5. A process of claim 2, wherein the molar fraction of dimethyl ether plus the molar fraction of methanol equals at least 0.95.

6. A process of claim 5 wherein, in the scrubbing solvent, the molar ratio of dimethyl ether to methanol is between 1/19 and 9.

7. A process of claim 6 wherein, in the scrubbing solvent, the molar ratio of dimethyl ether to methanol is between 1/4 and 1.

8. A process of claim 1 wherein the effluent mixture is processed in a post-reactor flash column so as to produce the vapor comprising dimethyl ether, carbon dioxide, and unconverted synthesis gas, and wherein said processing in the post-reactor flash column also produces a liquid comprising methanol, water, dissolved dimethyl ether and carbon dioxide.

9. A process of claim 8, said process further comprising:

directing a part or all of the liquid produced by the flash column to a methanol dehydration reactor;

producing a dehydration reactor mixture comprising dimethyl ether, carbon dioxide, methanol and water;

directing said dehydration reactor mixture to a post-dehydration flash column;

producing a vapor and a liquid in said post-dehydration flash column;

directing the vapor produced in said post-dehydration flash column to a DME-$CO_2$ column and therein separating DME of said vapor from $CO_2$ of said vapor;

directing the liquid produced in said post-dehydration flash column to a water-methanol column and therein separating methanol of said liquid from water of said liquid; and directing the methanol separated in the water-methanol column back to the methanol dehydration reactor.

10. A process of claim 8, said process further comprising directing a part or all of the liquid produced by the post-reactor flash column back to the dimethyl ether reactor.

11. A process of claim 1, wherein the unconverted synthesis gas separated in the scrubbing column is recycled to the dimethyl ether reactor.

12. A process of claim 1, wherein the scrubbing solvent that exits the scrubbing column is recycled back to the scrubbing column, after being directed through one or more additional columns.

13. A process of claim 1, the process further comprising:

directing the liquid stream from the scrubbing column to a post-scrubber flash column so as to produce a flash column vapor and a flash column liquid, said flash column vapor comprising dimethyl ether and carbon dioxide, said flash column liquid comprising a mixture of dimethyl ether and methanol, directing said flash column liquid to a solvent recovery column so as to produce a recovery column vapor and a recovery column liquid, said recovery column vapor comprising dimethyl ether and carbon dioxide, said recovery column liquid comprising a mixture of dimethyl ether and methanol, directing both the flash column vapor and the recovery column vapor to a DME-$CO_2$ column capable of separating DME from $CO_2$, and directing the recovery column liquid to the scrubbing column to so that said recovery column liquid becomes part of the scrubbing solvent in that column.

* * * * *